United States Patent [19]
Czech et al.

[11] Patent Number: 5,856,544
[45] Date of Patent: Jan. 5, 1999

[54] AMINOPOLYSILOXANES WITH HINDERED 4-AMINO-3,3-DIMETHYLBUTYL GROUPS

[75] Inventors: Anna Czech, Cortlandt Manor; Gerald J. Murphy, Hopewell Junction, both of N.Y.; Curtis L. Schilling, Jr., Marietta, Ohio

[73] Assignee: OSi Specialties, Inc., Greenwich, Conn.

[21] Appl. No.: 834,633

[22] Filed: Apr. 14, 1997

Related U.S. Application Data

[60] Provisional application No. 60/015,991 Apr. 15, 1996.

[51] Int. Cl.[6] .................................................. C07F 7/10
[52] U.S. Cl. ........................ 556/425; 428/365; 428/391; 427/411; 427/412; 427/415; 427/372.2; 106/124.8; 8/115.1; 8/115.6; 8/115.64; 8/196; 8/127.51; 8/128.7; 8/128.8; 8/DIG. 1; 424/70.122; 424/73; 510/122
[58] Field of Search ............................. 556/425; 428/365, 428/391; 427/411, 412, 415, 372.2; 106/124.8; 8/115.1, 115.6, 196, 127.51, 128.1, 128.3, 115.64, DIG. 1; 424/70.122, 73; 510/122

[56] References Cited

U.S. PATENT DOCUMENTS

| | | |
|---|---|---|
| 3,033,815 | 5/1962 | Pike et al. . |
| 3,146,250 | 8/1964 | Speier et al. . |
| 3,661,964 | 5/1972 | Griffiths et al. ..................... 556/425 |
| 4,098,701 | 7/1978 | Burrill et al. . |
| 4,152,346 | 5/1979 | Seiler et al. ........................ 556/425 |
| 4,247,592 | 1/1981 | Kalinowski . |
| 4,661,577 | 4/1987 | Jo Lane et al. . |
| 5,039,738 | 8/1991 | Czech . |
| 5,073,275 | 12/1991 | Ona et al. . |
| 5,354,880 | 10/1994 | Pepe et al. . |
| 5,391,400 | 2/1995 | Yang . |
| 5,486,634 | 1/1996 | Hahn et al. ........................ 556/425 |
| 5,496,401 | 3/1996 | Yang . |
| 5,567,752 | 10/1996 | Stein et al. ...................... 556/425 X |

FOREIGN PATENT DOCUMENTS

| | | |
|---|---|---|
| 0 577 039 A1 | 1/1994 | European Pat. Off. . |
| 0 692 567 A1 | 1/1996 | European Pat. Off. . |

OTHER PUBLICATIONS

Lautenschlager H.J. et al. "Struktur–Wirkungsbeziehung Aminofunktioneller Siliconweichmachungsmittel" Textil Praxis International, vol. 47, No. 5, 1 May 1992, pages.

*Primary Examiner*—Paul F. Shaver
*Attorney, Agent, or Firm*—Edward K. Welch, II; Andrew S. Reiskind; Timothy X. Witkowski

[57] ABSTRACT

Aminopolysiloxanes of the following structure $Q_2RSiO-(SiR_2O)_x-(SiRR^1O)_y-SiRQ_2$ wherein R is a monovalent hydrocarbon group having 1 to 10 carbon atoms including alkyl, aryl and aralkyl groups; $R^1$ is $CH_2-CH_2-C-(CH_3)_2-CH_2-NHR^2$, $R^2$ is hydrogen, an alkyl of $C_1-C_6$, an alkyl amine of $C_1-C_6$, or an alkanolamine of $C_1-C_6$; Q is R, $R^1$, hydroxyl, or an alkoxy of $C_1-C_4$. x can be zero or integer; y is an integer, with x+y being less than 1,100, for use in various applications, including softening textiles.

30 Claims, No Drawings

AMINOPOLYSILOXANES WITH HINDERED 4-AMINO-3,3-DIMETHYLBUTYL GROUPS

This application claims priority from U.S. Provisional Application Ser. No. 60/015,991, filed Apr. 15, 1996.

BACKGROUND

It is known to treat fibers and fabrics, both natural and synthetic, with organopolysiloxanes to impart tactile properties such as flexibility, smoothness and "hand". Among organopolysiloxanes, aminofunctional organopolysiloxanes have been recognized to provide the most desirable hand. Several examples of such aminoorganopolysiloxane can be found in the prior art.

U.S. Pat. No. 4,247,592 to Kalinowski teaches treating synthetic textiles with triorganosiloxy endblocked polydiorganosiloxanes having diamino groups attached through a lower alkylene to a mono or difunctional siloxy units. U.S. Pat. No. 4,661,577 to Lane discloses aminopolysiloxanes with trialkylsiloxy terminal groups having at least one amino, diamino or substituted amino group linked to at least one trifunctional siloxy unit through an alkylene bridge, which may also contain heteroatoms. U.S. Pat. No. 5,073,275 to Ona discloses a composition and method for treating organic fibers with a different type of aminoorganosiloxane, one modified with the SiC bonded N-cyclohexylaminoalkyl radicals.

SUMMARY OF THE INVENTION

The present invention provides novel aminofunctional polysiloxanes particularly useful in the treatment of textiles. These novel polysiloxanes contain hindered, 4-amino- 3,3-dimethylbutyl groups and can be reactive fluids with hydroxy, alkoxy or 4-amino- 3,3-dimethylbutyl terminal functionality or non-reactive, terminated with trialkylsiloxy groups. The polysiloxanes of the present invention contain hindered neohexylamino groups, which are less prone to oxidation and therefore cause less discoloration of any treated textiles. The present invention also provides methods for treating textiles with the aforesaid aminofunctional silicone compositions.

The present invention is directed to polysiloxanes of general formula (I)

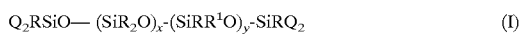

$$Q_2RSiO-(SiR_2O)_x-(SiRR^1O)_y-SiRQ_2 \qquad (I)$$

wherein

R is selected from the group consisting of monovalent hydrocarbon groups having 1 to 10 carbon atoms including alkyl, aryl and aralkyl groups. The R groups may be the same or different from one another and are illustrated by methyl, ethyl, butyl, hexyl, phenyl, benzyl and phenethyl. Of these, lower alkyl groups ($C_1-C_4$) are preferred. Most preferably R is methyl.

$R^1$ is $CH_2CH_2C(CH_3)_2CH_2N(R^2)_2$, where each $R^2$ is the same or different and each is hydrogen, an alkyl of $C_1-C_6$, an alkyl amine of $C_1-C_6$ (i.e. a $C_1-C_6$ alkyl group substituted with —$NH_2$) or an alkanolamine of $C_1-C_6$ (i.e. a $C_1-C_6$ alkyl group substituted with —OH and with —$NH_2$). Specific $R^2$ groups include propylamine, propanolamine, methyl, and most preferably, hydrogen. The amino group on $R^1$ may be protonated or quaternized.

Q is R, $R^1$, hydroxyl, or an alkoxy of $C_1-C_4$. Preferably, the alkoxy group is methoxy or ethoxy. Most preferably Q is methyl.

"x" can be zero or an integer; "y" is an integer greater than zero (with the understanding that for an overall polysiloxane composition, x and y represent average numbers), with x+y being less than 1,100. Preferably x ranges from 20 to 1000 and y ranges from 1 to 50; most preferably x ranges from 50 to 800 or 50 to 500 and y ranges from 1 to 20.

DETAILED DESCRIPTION OF THE INVENTION

Aminopolysiloxanes of the present invention are prepared, for example, by processes analogous to those disclosed in U.S. Pat. Nos. 3,033,815, 3,146,250 and 4,247,592 (which are incorporated by reference) by hydrolyzing the corresponding dialkoxy 4-amino-3,3-dimethylbutyl modified silane (which can be prepared according to U.S. Pat. No. 5,354,880 to Pepe, which is incorporated herein by reference) in excess water or water-solvent such as tetrahydrofuran mixture, at 10° to 50° C., preferably, room temperature, for 2 to 5 hours followed by vacuum strip and equilibrating the resulting hydrolyzate with di(alkyl, aralkyl or aryl)cyclopolysiloxane (source of $R_2SiO$ groups) and hexamethyldisiloxane, decamethyltetrasiloxane, or other reactants to serve as the source of the terminal $RQ_2SiO$ groups as defined by Formula I) in the presence of a base catalyst, such as KOH, with heating at about 130° to 150° C. for about 5 to 12 hours. A reactive aminopolysiloxane having hydroxy or alkoxy terminal groups can be prepared in a similar and well known manner from the amine containing silane and cyclopolysiloxane.

The protonated form of the polysiloxanes can be prepared by adding a protonic acid in an amount calculated to achieve the desired degree of protonation, that is, complete or less than complete if the amount of acid added is less than stoichiometric. The quaternized form of the polysiloxane can be prepared by reacting it with a suitable quaternizing agent, such as methyl chloride, benzyl chloride, dimethyl sulfate, or diethyl sulfate. Preferred quaternary substituents include methyl, ethyl, and benzyl. The quaternary forms of the polysiloxane will be in ionic neutrality with a stoichoimetric amount of an anion such as chloride, methylsulfate or ethylsulfate.

While the aminopolysiloxanes of the present invention can be used neat, for ease of the application, they are usually applied dissolved, dispersed or emulsified in a suitable liquid medium. Preferably, the aminopolysiloxanes of the present invention can be applied from an aqueous solution, emulsion or dispersion. The aminopolysiloxanes may also be applied as a solution in a nonaqueous solvent such as isopropanol and hexane, or in a liquid in which the aminopolysiloxane is miscible, such as, toluene. Most preferably, the aminopolysiloxane is applied to the textile as an aqueous emulsion.

The preparation of aqueous emulsions of aminopolysiloxanes is well known to those skilled in the art. One such preparation is described, for example, in U.S. Pat. No. 5,039,738, which is incorporated herein by reference. To prepare an aqueous emulsion, an aminopolysiloxane is optionally combined with emulsifiers known in the art and diluted to the desired polymer level with water. The polymer content of the aminopolysiloxane emulsion of the present invention ranges from about 10 to 80 percent, preferably 20 to 40 percent.

The emulsion of the aminopolysiloxane of the present invention can be applied to the surface of any desired substrate, such as by spraying, dipping, or kiss roll application. The polysiloxane should be applied so that the amount of polysiloxane is 0.1 to 5.0, preferably 0.2 to 2.5, weight percent of the textile.

Substrates which can be treated with the aminopolysiloxanes of the present invention include textiles (both woven and nonwoven), hair, and paper. Textiles are exemplified by (I) natural fibers such as cotton, flax, wool and silk; (ii) synthetic fibers such as polyester, polyamide, polyacrylonitrile, polyethylene, polypropylene and polyurethane; (iii) inorganic fibers such as glass and carbon fiber; or (iv) blends of any of the above-mentioned fibers.

Optionally, other additives typically employed in treating the textile or other substrate can be included with the emulsion or applied separately to the substrate. Such additives can include a durable press resin, curing catalyst, preservatives and biocides, pigments or dyes, fragrances, fillers, pH buffers, antifoamer and defoamers.

Textiles and other substrates treated with the aminopolysiloxane of the present invention are dried either at room temperature or by heat and cured at a temperature less than the melting or decomposition temperature of the substrate. Heating can be accomplished by any suitable method, but preferably is done by passing the substrate through a hot air oven. The resulting treated substrate, thus, has properties such as amine-like hand and whiteness.

Moreover, compositions including the amino polysiloxanes of the present invention may be used in personal care formulations, including lotions, creams, shaving cream, hair sprays, conditioners, shampoos, deodorants, moisturizers, and sunblocks, and in adhesive and sealant formulations. Additionally, said aminpolysiloxanes may be used in car wax formulations.

EXAMPLES

The following specific examples are set forth for illustration only and are not to be construed as limiting of the present invention.

In the examples, the test fabric and test procedures used were as follows:

Fabrics Identification (Test Fabrics Inc. Middlesex N.J.)— Bleached Cotton Interlock Knit, Style 460; Bleached Desized Cotton Print Cloth, Style 400.

Test Procedures
  Conditioning Textiles for Testing, ASTM Method D-1776-79
  Absorbency of Bleached Textiles, AATCC Method 79-1992
  Softness evaluation was done by the hand panel and the tested fabrics were rated on the scale from 1 to 10, where 1 is very harsh 10 is very soft. Each hand panel involved at least five panelists and reported results are average values.
  To evaluate discoloration of the treated textiles caused by the aminopolysiloxanes, whiteness/reflectance data were generated using Colorquest Colorimeter from Hunter Labs.
  Reflectance of the fabrics scorched in the curing oven at 200° C. for 100 seconds was measured to determine resistance of the aminosilicone finishes to prolonged heating.

EXAMPLE 1
Preparation of Aminopolysiloxanes Emulsions

The aminopolysiloxanes set forth in Table 1 were prepared in accordance with the procedure disclosed in U.S. Pat. No. 2,247,592, using 4-amino-3,3-dimethylbutylmethyldimethoxysilane as a source of aminofunctionality, and formulated into emulsions. To form an emulsion, 40 parts of the aminopolysiloxane was mixed in a vessel with a surfactant blend of 3.6 parts of TERGITOL® 15-S-3 surfactant, 2.4 parts of TERGITOL® 15-S-15 surfactant and 12 parts water to form a premix. The premix was homogenized with a laboratory mixer at 500 to 800 rpm. The remaining water (42 parts) was added slowly while mixing.

TABLE 1

4-Amino-3,3-dimethylbutyl Modified Polysiloxanes

| Designation | Formula[1] | Viscosity (cps) | Amine Content (as wt % $NH_2$)[2] |
|---|---|---|---|
| Aminopolysiloxane I   | $MD_{50}D^*_2M$    | 105  | 0.82 |
| Aminopolysiloxane II  | $MD_{100}D^*_2M$   | 216  | 0.42 |
| Aminopolysiloxane III | $MD_{250}D^*_5M$   | 1404 | 0.43 |
| Aminopolysiloxane IV  | $MD_{250}D^*_{10}M$| 1056 | 0.88 |
| Aminopolysiloxane V   | $MD_{500}D^*_3M$   | 4632 | 0.15 |
| Aminopolysiloxane VI  | $MD_{500}D^*_6M$   | 3690 | 0.29 |

[1] $M = O_{1/2}Si(CH_3)_3$; $D = OSi(CH_3)_2$; $D^* = OSiCH_2CH_2C(CH_3)_2CH_2NH_2$
[2] Amine content determined by titration These polysiloxanes were applied to 100% cotton, knit and woven, with and without durable press resin at 1.0 weight percent of polysiloxane. The polysiloxanes improved the hand of the fabric with minimal yellowing after curing.

EXAMPLE 2

Softness and Discoloration of 100% Cotton Knit Treated with 4-Amino-3,3-dimethylbutyl Modified Polysiloxanes Aminopolysiloxanes I-VI as set forth in Table 1, and two control softeners MAGNASOFT® Ultra and MAGNASOFT® PLUS (commercial premium amino softeners modified with 3-(2-(aminoethyl)aminopropyl pendant groups, having amine content of 0.8% and 0.25% as $NH_2$, respectively) were padded onto 100% cotton knit in combination with a durable press resin (methylated dimethyloldihydroxyethyleneurea, which is commercially available) and curing catalyst (magnesium chloride) to simulate typical textile finishing procedure. The softener concentration in the finishing composition was such that the effective actives add-on levels on the fabric were 1.0% (BOWF, i.e., based on the weight of the fabric); curing conditions were 171° C. for 1.5 minutes. Softness and reflectance data are provided in Table 2.

TABLE 2

Softness and Reflectance of 100% Cotton Knit Treated with 4-Amino-3,3-dimethylbutyl Modified Polysiloxanes

| Designation/ Amine Content as $NH_2$ | Softness Rating[1] | Reflectance[2] |
|---|---|---|
| Magnasoft ® Ultra (0.80%)     | 9.0 | 64.4 |
| Magnasoft ® Plus (0.25%)      | 7.8 | 72.5 |
| Aminopolysiloxane I (0.82%)   | 3.0 | 72.6 |
| Aminopolysiloxane II (0.42%)  | 6.5 | 74.2 |
| Aminopolysiloxane III (0.43%) | 7.3 | 75.3 |
| Aminopolysiloxane IV (0.88%)  | 5.8 | 72.8 |
| Aminopolysiloxane V (0.15%)   | 5.1 | 80.1 |

TABLE 2-continued

Softness and Reflectance of 100% Cotton Knit Treated
with 4-Amino-3,3-dimethylbutyl Modified Polysiloxanes

| Designation/ Amine Content as $NH_2$ | Softness Rating[1] | Reflectance[2] |
|---|---|---|
| Aminopolysiloxane VI (0.29%) | 6.6 | 79.6 |
| Resin only | 1.0 | 83.9 |

[1]rated on the scale 1–10, where 1 is harsh and 10 is very soft
[2]higher numbers mean lower discoloration All 4-amino-3,3-dimethylbutyl modified polysiloxanes improved the hand of 100% cotton knit fabrics and, at the equivalent amine content, caused less discoloration of the textile substrate than aminopolysiloxanes modified with 3-(2-aminoethyl)aminopropyl groups.

EXAMPLE 3

Softness and Discoloration of 100% Cotton Woven Treated with 4-Amino-3,3-dimethylbutyl Modified Polysiloxanes Aminopolysiloxanes I-VI, as set forth in Table 1, and two control softeners MAGNASOFT® Ultra and MAGNASOFT® PLUS (commercial premium amino softeners modified with 3-(2-aminoethyl)aminopropyl pendant groups, having amine content of 0.8% and 0.25% as $NH_2$, respectively) were padded onto 100% cotton print cloth in combination with a durable press resin (methylated dimethyloldihydroxyethyleneurea, which is commercially available) and curing catalyst (magnesium chloride) to simulate typical textile finishing procedure. The softener concentration in the finishing composition was such that the effective actives add-on levels on the fabric were 1.0% (BOWF); curing conditions were 171° C. for 1.5 minutes. Softness and reflectance data are given in Table 3.

TABLE 3

Softness and Reflectance of 100% Cotton Print Cloth Treated with 4-Amino-3,3-dimethylbutyl Modified Polysiloxanes

| Designation/ Amine Content as $NH_2$ | Softness Rating[1] | Reflectance[2] |
|---|---|---|
| Magnasoft ® Ultra (0.8%) | 6.6 | 53.0 |
| Magnasoft ® Plus (0.25%) | 8.0 | 58.4 |
| Aminopolysiloxane I (0.82%) | 8.2 | 56.4 |
| Aminopolysiloxane II (0.42%) | 7.1 | 57.4 |
| Aminopolysiloxane III (0.43%) | 5.3 | 60.0 |
| Aminopolysiloxane IV (0.88%) | 6.7 | 57.6 |
| Aminopolysiloxane V (0.15%) | 8.2 | 63.2 |
| Aminopolysiloxane VI (0.29%) | 6.4 | 62.4 |
| Resin Only | 1.0 | 64.2 |

[1]rated on the scale 1–10, where 1 is harsh and 10 is very soft
[2]higher numbers mean lower discoloration All 4-amino-3,3-dimethylbutyl modified polysiloxanes improved the hand of 100% cotton knit fabrics and, at the equivalent amine content, caused less discoloration of the textile substrate than aminopolysiloxanes modified with 3-(2-aminoethyl)aminopropyl groups.

EXAMPLE 4

Reflectance of the Scorched 100% Cotton Print Cloth Fabrics Treated with 4-Amino-3,3-dimethylbutyl Modified Polysiloxanes Reflectance of the treated fabrics from Example 3, exposed to scorch conditions at 200° C. for 100 seconds, has been measured to determine yellowing tendency of the inventive polysiloxanes under prolonged heat. Results are summarized in Table 4.

TABLE 4

Reflectance of the Scorched 100% Print Cloth Treated with with 4-Amino-3,3-dimethylbutyl Modified Polysiloxanes

| Designation/ Amine Content as $NH_2$ | Reflectance after scorching[1] |
|---|---|
| Magnasoft ® Ultra (0.8%) | 26.7 |
| Magnasoft ® Plus (0.25%) | 35.7 |
| Aminopolysiloxane I (0.82%) | 32.0 |
| Aminopolysiloxane II (0.42%) | 33.5 |
| Aminopolysiloxane III (0.43%) | 32.6 |
| Aminopolysiloxane IV (0.88%) | 31.8 |
| Aminopolysiloxane V (0.15%) | 38.1 |
| Aminopolysiloxane VI (0.29%) | 37.4 |
| Resin Only | 39.5 |

[1]higher numbers mean lower discoloration

At the equivalent amine content, 4-amino-3,3-dimethylbutyl modified polysiloxanes caused less discoloration of the textile substrate than aminopolysiloxanes modified with 3-(2-aminoethyl)aminopropyl groups.

What is claimed is:

1. A polysiloxane of the formula (I)

$$Q_2RSiO-(SiR_2O)_x-(SiRR^1O)_y-SiRQ_2 \quad (I)$$

wherein
each R group is the same or different and each is selected from the group consisting of monovalent alkyl, aryl and aralkyl hydrocarbon groups having 1 to 10 carbon atoms;
$R^1$ is $CH_2CH_2C(CH_3)_2CH_2N(R^2)_2$, wherein each $R^2$ is the same or different and each is hydrogen, a $C_1$–$C_6$ alkyl group, a $C_1$–$C_6$ alkyl amine group, or a $C_1$–$C_6$ alkanolamine group, and each nitrogen atom in an $R^1$ group is optionally protonated or quaternized;
Q is R, $R^1$, hydroxyl, or a $C_1$–$C_4$ alkoxy group;
x is zero or an integer; y is an integer greater than zero, and the sum of (x+y) is less than 1100.

2. A polysiloxane according to claim 1 wherein each R group is selected from the group consisting of phenyl, benzyl, phenethyl, and $C_1$–$C_6$ alkyl groups.

3. A polysiloxane according to claim 1 wherein each R group is methyl.

4. A polysiloxane according to claim 3 wherein $R^2$ is hydrogen.

5. A polysiloxane according to claim 1 wherein $R^2$ is hydrogen.

6. A polysiloxane according to claim 1 wherein each Q is methoxy or ethoxy.

7. A polysiloxane according to claim 1 wherein each Q is methyl.

8. A polysiloxane according to claim 3 wherein each Q is methyl.

9. A polysiloxane according to claim 1 wherein each Q is an $R^1$ group.

10. A polysiloxane according to claim 1 wherein x is 20 to 1,000.

11. A polysiloxane according to claim 1 wherein y is 1 to 20.

12. A liquid composition in which a polysiloxane according to claim 1 is dissolved, dispersed or emulsified.

13. A liquid composition in which a polysiloxane according to claim 3 is dissolved, dispersed or emulsified.

14. A liquid composition in which a polysiloxane according to claim 4 is dissolved, disperse or emulsified.

15. A liquid composition in which a polysiloxane according to claim 8 is dissolved, dispersed or emulsified.

16. A method of treating a substrate selected from the group consisting of woven and nonwoven textiles, hair and paper, comprising applying thereto a polysiloxane according to claim 1.

17. A method according to claim 16 comprising applying an aqueous emulsion of said polysiloxane.

18. A method of treating a substrate selected from the group consisting of woven and nonwoven textiles, hair and paper, comprising applying thereto a polysiloxane according to claim 3.

19. A method according to claim 18 comprising applying an aqueous emulsion of said polysiloxane.

20. A method of treating a substrate selected from the group consisting of woven and nonwoven textiles, hair and paper, comprising applying thereto a polysiloxane according to claim 4.

21. A method according to claim 20 comprising applying an aqueous emulsion of said polysiloxane.

22. A method of treating a substrate selected from the group consisting of woven and nonwoven textiles, hair and paper, comprising applying thereto a polysiloxane according to claim 8.

23. A method according to claim 22 comprising applying an aqueous emulsion of said polysiloxane.

24. A method of treating a substrate selected from the group consisting of woven and nonwoven textiles, hair and paper, comprising applying thereto a polysiloxane according to claim 9.

25. A method according to claim 24 comprising applying an aqueous emulsion of said polysiloxane.

26. A substrate selected from the group consisting of woven and nonwoven textiles, hair and paper, to at least one surface of which a polysiloxane according to claim 1 has been applied.

27. A substrate selected from the group consisting of woven and nonwoven textiles, hair and paper, to at least one surface of which a polysiloxane according to claim 3 has been applied.

28. A substrate selected from the group consisting of woven and nonwoven textiles, hair and paper, to at least one surface of which a polysiloxane according to claim 4 has been applied.

29. A substrate selected from the group consisting of woven and nonwoven textiles, hair and paper, to at least one surface of which a polysiloxane according to claim 8 has been applied.

30. A substrate selected from the group consisting of woven and nonwoven textiles, hair and paper, to at least one surface of which a polysiloxane according to claim 9 has been applied.

* * * * *